US007772374B2

(12) United States Patent
Mangold et al.

(10) Patent No.: US 7,772,374 B2
(45) Date of Patent: Aug. 10, 2010

(54) SPORE SPECIFIC ANTIBODIES

(75) Inventors: Beverly L. Mangold, Rockville, MD (US); Jennifer L. Aldrich, Frederick, MD (US)

(73) Assignee: Tetracore, Inc., Gaithersburg, MD (US)

( * ) Notice: Subject to any disclaimer, the term of this patent is extended or adjusted under 35 U.S.C. 154(b) by 1072 days.

(21) Appl. No.: 11/127,435

(22) Filed: May 11, 2005

(65) Prior Publication Data

US 2006/0286612 A1 Dec. 21, 2006

Related U.S. Application Data

(60) Provisional application No. 60/570,798, filed on May 12, 2004.

(51) Int. Cl.
*C07K 16/00* (2006.01)

(52) U.S. Cl. ............... 530/388.1; 530/388.2; 530/387.1

(58) Field of Classification Search ....................... None
See application file for complete search history.

(56) References Cited

U.S. PATENT DOCUMENTS 6,913,756 B1 7/2005 Kearney

FOREIGN PATENT DOCUMENTS

WO WO0183561 A2 * 11/2001
WO WO03/103481 A2 12/2003

OTHER PUBLICATIONS

Nosoh, Y. et al in "Protein Stability and Stabilization through Protein Engineering, 1991".*

Thomas E. Creighton, "Protein Structure: A Practical Approach, 1989; pp. 184-186".*

Thomas E. Creighton, "Proteins: Structures and Molecular Properties, 1984", (pp. 314-315).*

Hill, Karen K., et al. "Fluorescent Amplified Fragment Length Polymorphism Analysis of *Bacillus anthracis, Bacillus cereus*, and *Bacillus thuringiensis* Isolates", *Applied and Environmental Microbiology* (2004) 70(2):1068-1080.

Hoffmaster, Alex R., et al. Identification of anthrax toxin genes in a *Bacillus cereus* associated with an illness resembling inhalation anthrax, *PNAS* (2004) 101(22):8449-8454.

Chen, Yinghua, et al. "A Novel Spore Peplidoglycan Hyrolase of *Bacillus cereus*: Biochemical Characterization and Nucleotide Sequence of the Corresponding Gene, *sleL" Journal of Bacteriology* (2000) 182(6):1499-1506.

Shimamoto, Seiko, et al. "Partial Characterization of an Enzyme Fraction with Protease Activity Which Converts the Spore Peptidoglycan Hydrolase (SleC) Precursor to an Active Enzyme during Germination of *Clostridium perfringens* S40 Spores and Analysis of a Gene Cluster Involved in the Activity", *Journal of Bacteriology* (2001) 183(12):3742-3751.

Chen, Yinghua, et al. "Molecular Characterization of a Germination-Specific Muramidase from *Clostridium perfringens* S40 Spores and Nucleotide Sequence of the Corresponding Gene", *Journal of Bacteriology* (1997) 179(10):3181-3187.

Keim, P., et al "Multiple-Locus Variable-Number Tandem Repeat Analysis Reveals Genetic Relationships within *Bacillus anthracis", Journal of Bacteriology* (2000) 182(10):2928-2936.

Dang, Jessica I., et al. "*Bacillus* Spore Inactivation Methods Affect Detection Assays", *Applied and Environmental Microbiology* (2001) 67(8):3665-3670.

Williams, David D., et al. Surface Layer Protein EA1 Is Not a Component of *Baccillus anthracis* Spores but is a Persistent Contaminant in Spore Preparation, *Journal of Bacteriology* (2004) 186(2):566-569.

Sequence Alignment AC# Q9K3E4 (see under result 12).

Brettin et al., Database GenBank NCBI; retrieved from http://www.ncbi.nlm.gov Database Accession No. YP_029658.

Fox et al., "Carbohydrates and Glycoproteins of *B. anthracis* and related bacilli: Targets for Biodetection," J. Microbiol. Meth., 54:143-152 (2003).

Han et al., Database GenBank NCBI; retrieved from http://www.ncbi.nlm.gov Database Accession No. YP_037686 (2004).

Han et al., Database GenBank NCBI; retrieved from http://www.ncbi.nlm.gov, Database Accession No. YP_084899 (2005).

Lai et al., "Proteomic Analysis of the Spore Coats of *B. subtilis* and *B. anthracis*," J. Bacteriol., 185(4):1443-1454 (Feb. 2003).

Longchamp and Leighton, "Molecular Recognition Specificity of *B. anthracis* spore antibodies," J. Appl. Micro. 87:246-249 (1999).

Read et al., Database GenBank NCBI; retrieved from http://www.ncbi.nlm.gov, Database Accession No. ZP_00393845 (2005).

Todd et al., "Genes of *B. cereus* and *B. anthracis* Encoding Proteins of the Exosporium," J. Biol. 185(11): 3373-3378 (Jun. 2003).

* cited by examiner

*Primary Examiner*—Robert Mondesi
*Assistant Examiner*—Khatol Shahnan-Shah
(74) *Attorney, Agent, or Firm*—Patentique, PLLC

(57) ABSTRACT

The invention relates to spore specific antibodies. Compositions and methods relating to the antibodies are provided along with the hybridomas that produce the antibodies. The antibodies are specific for the spores of *Bacillus anthracis* relative to the vegetative form of the cells. The antibodies are also specific for the spores relative to other *Bacillus* spores and cells. The antibodies may be used to detect the presence of *Bacillus anthracis* spores by use of methods provided herein. The invention also relates to articles of manufacture as well as kits comprising these antibodies which may be used in the detection methods of the invention.

19 Claims, 3 Drawing Sheets

SPORE SPECIFIC ANTIBODIES

RELATED APPLICATIONS

This application claims benefit of priority to U.S. Provisional Application 60/570,798, filed May 12, 2004, which is hereby incorporated by reference in its entirety as if fully set forth.

FIELD OF THE INVENTION

This invention relates to spore specific antibodies. The invention provides compositions and methods relating to the antibodies as well as the hybridomas that produce them. The antibodies of the invention are specific for the spores of *B. anthracis* relative to the vegetative form of the cells. The antibodies are also specific for the spores relative to other *Bacillus* spores and cells. The antibodies may be used to detect the presence of *B. anthracis* spores by use of methods provided herein. The invention also relates to articles of manufacture as well as kits comprising these antibodies which may be used in the detection methods of the invention.

BACKGROUND OF THE INVENTION

*Bacillus anthracis*, the causative agent of anthrax, is a spore-forming, Gram-positive, non-hemolytic, rod-shaped bacterium. Anthrax is primarily a zoonotic disease of herbivores; however, humans can naturally acquire this disease directly from contact with infected herbivores, or indirectly via their products, such as hair, wool, and hides. Spores are the usual infective form. Anthrax presents clinically as three distinct syndromes, depending on the route of infection: cutaneous, gastrointestinal, and inhalational disease. Cutaneous anthrax is the most common naturally occurring form in humans. However, inhalational anthrax, although seen only rarely in naturally acquired infections, would be the major concern in a situation involving the release of aerosolized spores. Such was demonstrated by the accidental release of aerosolized spores from Sverdlovsk in the former Soviet Union in 1979 (Meselson et al 1994) and the intentional release of aerosolized spores in the anthrax letter attacks in the United States in October 2001 (Jernigan et al., 2001). The high level of mortality seen with inhalational anthrax can be mitigated by administration of the appropriate antibiotics within 24-48 hours of exposure. However, delays in administrating antibiotics beyond 24-48 hours of exposure generally results in death to individuals receiving a lethal dose of spores.

The spore coat and exosporium of *B. anthracis* have been the focus of previous studies. When *B. anthracis* vegetative cells are deprived of essential nutrients ("starved"), a trigger is given to begin synthesis of the endospore ("spore"). The following sequence of events takes place when the vegetative cells are starved: 1) an asymmetric septation of starved vegetative cells occurs, resulting in the formation of the mother cell and a forespore; 2) the mother cell engulfs the forespore, thus surrounding the forespore with two opposing cell membranes; 3) a thick layer of modified peptidoglycan ("cortex") is synthesized between the two membranes; and 4) proteins synthesized in the mother cell form multiple layers of a spore coat that covers the cortex.

The spore coat forms the outermost layer for spores of some *Bacillus* species, such as *B. subtilis*. However, in other species, such as *B. anthracis*, the spore is enclosed by an additional layer called the exosporium, a loose balloon-like layer containing proteins, lipid, and carbohydrate. Charlton et al. ("Characterization of the exosporium of *Bacillus cereus*" *J. App. Microbiol.* 87:241-245, 1999) describe studies on the exosporium of *B. cereus*. Spores of the closely related species *B. thuringiensis* also have an exosporium. A number of investigators have previously identified spore coat and exosporium antigens of *B. anthracis*. Lai et al. ("Proteomic analysis of the spore coats of *Bacillus subtilis* and *Bacillus anthracis*" *J. Bact.*, (185(4):1443-1454, 2003), using proteomic analysis employing a combination of SDS-PAGE separation and 2-D 313ctrophoretic separations, followed by matrix-assisted laser desorption ionization-time of flight (MALDI-TOF®), identified 38 spore proteins of *B. subtilis* (of which 12 are known spore coat proteins) and 11 spore proteins of *B. anthracis* (6 of which they identified as candidate coat or exosporium proteins). From their studies comparing *B. subtilis* and *B. anthracis* spore proteins, Lai et al. concluded that "*B. subtilis* and *B. anthracis* coats have roughly similar numbers of proteins and that a core group of coat protein species is shared between these organisms, including the major morphogenetic proteins. Nonetheless, a significant number of coat proteins are probably unique to each species" (underlining added; see Lai et al. abstract).

Steichen et al. ("Identification of the immunodominant protein and other proteins of the *Bacillus anthracis* exosporium", *J. Bact.*, 185(6):1903-1910, 2003) identified five major proteins in purified *B. anthracis* exosporium, including the collagen-like-glycoprotein BclA, which they described as a structural component of the exosporium hair-like nap. These investigators concluded that BclA is the immunodominant antigen on the *B. anthracis* spore surface because 12 out of 20 monoclonal antibodies raised against either spores or purified exosporium reacted with BclA. The other four proteins identified by Steichen et al. are alanine racemase, superoxide dismutase, and two proteins with no significant similarity to any other protein, which they called BxpA and BxpB.

In addition, Todd et al. ("Genes of *Bacillus cereus* and *Bacillus anthracis* encoding proteins of the exosporium", *J. Bact.*, 185(11):3373-3378, 2003) evaluated exosporium proteins of *B. cereus*. *B. cereus* is a member of the *Bacillus cereus* family, which includes *B. thuringiensis* and *B. anthracis*, all of which possess an exosporium and all of which are close relatives. Other related *Bacillus* species include *B. subtilis, B. globigii, B. pumilis, B. mycoides*, and *B. megaterium*. Todd et al. identified 10 exosporium proteins of *B. cereus*. They concluded, based on a comparative analysis of *B. cereus* protein sequences with predicted protein sequences from the *B. anthracis* genome sequences that "[f]rom the available unfinished genome sequences, most of the novel Exs proteins are closely conserved between *B. cereus* and *B. anthracis*, with two exceptions . . . a local region of ExsB and the entire ExsC protein that may not be expressed in *B. anthracis*." (see page 3378, first full paragraph). They further note that their "identified genes do not by any means represent an exhaustive list of protein components of the exosporium; one-third of protein remained in the insoluble fraction, and 7 out of 17 bands have not yielded clear N-terminal sequence data." (see page 3378, fourth full paragraph).

In the literature concerning spore coat or exosporium proteins of *B. anthracis*, the only monoclonal antibodies developed were to the immunodominant *Bacillus* collagen-like protein of anthracis, BclA (see Sylvestre et al., "A collagen-like surface glycoprotein is a structural component of the *Bacillus anthracis* exosporium" *Molec. Microbiol.* 45(1):169-178, 2002; and Steichen et al.). The spore specific monoclonal antibody of the instant invention as described herein does not react with this protein. Longchamp et al. ("Molecular recognition specificity of *Bacillus anthracis* spore antibodies" *J. App. Microbiol.* 87:246-249, 1999) describe the characterization of polyclonal serum which recognized a wide range of spore surface epitopes which cross-reacted with related *Bacillus* species. They further describe two monoclonal antibodies that did not react with spore surface epitopes. Lee et al. (WO 01/49823) describe antibodies against a *B. anthracis* surface array protein, to which the 23a-14G9 monoclonal antibody of the instant invention as described below does not react.

Citation of documents herein is not intended as an admission that any is pertinent prior art. All statements as to the date or representation as to the contents of documents is based on the information available to the applicant and does not constitute any admission as to the correctness of the dates or contents of the documents.

BRIEF SUMMARY OF THE INVENTION

The invention relates to monoclonal and polyclonal antibodies that are specific for the spores of *B. anthracis* relative to the vegetative or actively growing forms of that organism as well as related *Bacillus* species. The antibodies may be advantageously used in a method, procedure, assay or test to rapidly detect and identify *B. anthracis* spores in an accurate and specific fashion.

In a first aspect, the invention provides a murine monoclonal antibody identified as 23a-14G9, which binds to a *B. anthracis* spore specific antigen. The antibody is specific for the spores of *B. anthracis* relative to the vegetative form of the cells. The antibodies are also specific for the spores relative to other *Bacillus* spores and cells.

The invention also provides alternative forms of the monoclonal antibody, including, but not limited to, binding fragments of the antibody as well as hybrid, chimeric, altered, recombinant, or humanized forms of the antibody which bind the spores of *B. anthracis*. Non-limiting examples of antibody fragments include bivalent $F(ab')_2$ fragments, such as those produced by digestion with pepsin, and monovalent Fab fragments, such as those produced by digestion with papain.

In a second aspect, the invention provides additional monoclonal and polyclonal antibodies that bind the same spore specific antigen as 23a-14G9. These additional antibodies may be produced by routine methods known in the field, without a need for knowledge regarding the identity of the spore specific antigen. One means is by use of a complex comprising the spore specific antigen and 23a-14G9 as an immunogen to produce additional antibodies. These initial antibodies may be used to generate hybridoma cells that express each antibody as a monoclonal. The hybridomas may then be screened or otherwise selected to identify those that express a monoclonal antibody that binds/recognizes the spore specific antigen and not the 23a-14G9 antibody. The identified antibodies are specific for the spore specific antigen and are antibodies of the invention that may be used or applied in the same manner as 23a-14G9 as described herein. The identified antibodies may also be used individually to form additional complexes with the spore specific antigen to produce additional antibodies which are then again screened or selected for those which are specific for the antigen rather than the antibody used in the complex.

In another aspect, the invention also provides for compositions comprising the monoclonal and polyclonal antibodies as well as the alternative forms thereof. The compositions include articles of manufacture, as well as kits, comprising one or more of the antibodies and alternative forms thereof. The compositions may further comprise one or more other reagent for the detection of *B. anthracis* or other *Bacillus* species. Non-limiting examples of articles of manufacture include test devices like plates, dishes, and wells for the detection of *B. anthracis*. Kits of the invention include those comprising other reagents used in the detection of *B. anthracis*. Non-limiting examples include those suitable for use with the detection methods described herein.

In yet another aspect, the invention provides for methods to detect the presence of *B. anthracis* spores by use of the antibodies and alternative forms thereof as disclosed herein. The methods of the invention are not limited by format or design. The methods may be conducted qualitatively or quantitatively to detect *B. anthracis*. As one exemplary embodiment, the invention provides a method to detect the presence or absence of *B. anthracis* spores in a sample, such as a medical sample of material obtained from a subject, including from the skin or clothing of the subject. Alternatively, the sample may be an environmental sample, such as a soil or air sample, or a sample of material suspected of containing spores, such as suspicious powders. The method comprises detecting the binding of an antibody of the invention, or an alternative form thereof, to a component of said sample to form a bound complex. The binding results from contact of the antibody, or an alternative form thereof, with the component, which is the *B. anthracis* antigen bound by the antibody.

The invention further provides a hybridoma cell that produces the 23a-14G9 antibody. The cell was deposited with the ATCC (10801 University Blvd., Manassas, Va. 20110) on May 19, 2004 and identified by ATCC accession number PTA-6004. The hybridoma may be cultured in vitro to produce antibodies for use as disclosed herein, after an optional purification or isolation step. Alternatively, the hybridoma may be introduced into an animal to form an ascites from which antibody containing fluid may be obtained. The resultant antibodies may be used as disclosed herein, after an optional purification or isolation step.

DETAILED DESCRIPTION OF MODES OF PRACTICING THE INVENTION

Figure 1:
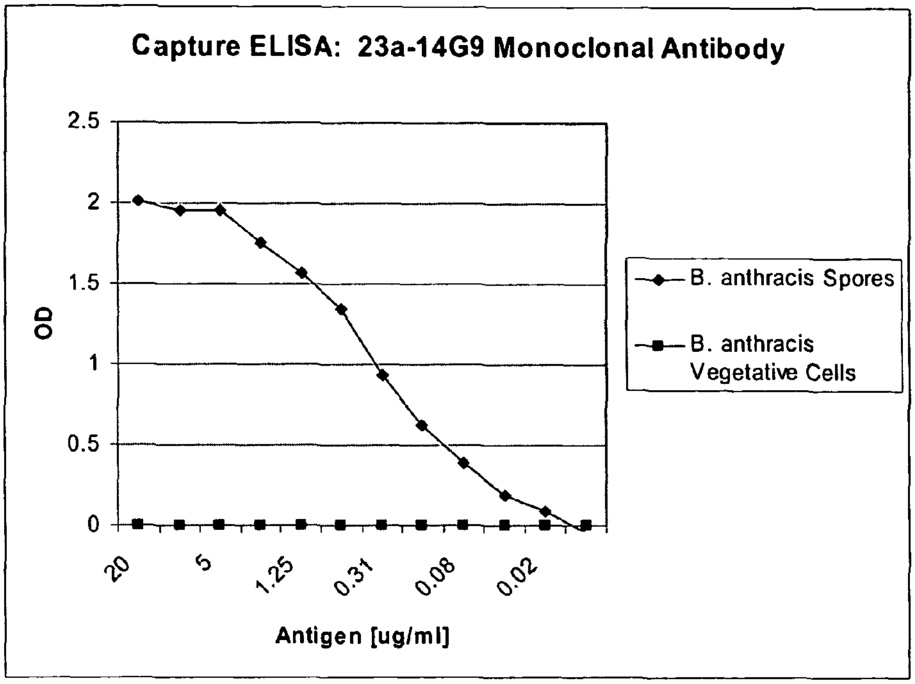
FIG. 1 shows the specificity of 23a-14G9 for *B. anthracis* spores relative to vegetative cells in a capture ELISA assay.

The invention is directed to antibodies that bind and recognize a *B. anthracis* spore specific antigen. The antibodies of the invention include both polyclonal and monoclonal antibodies that recognize the spore specific antigen to the exclusion of other *B. anthracis* antigens present in *B. anthracis* spores. The antibodies may also recognize the antigen to the exclusion of other antibodies that bind the antigen. A complex comprising an antibody bound to the spore specific antigen is also provided by the invention. The complex may be one that is isolated or immobilized as described herein.

This invention also provides a murine monoclonal antibody identified as 23a-14G9, which is specific for the spores of *B. anthracis* relative to the vegetative form of the cells. The antibody, as well as *B. anthracis* antigen binding forms thereof, may thus be used to differentially detect *B. anthracis* spores from vegetative cells. The antibody is also specific for spores of *B. anthracis* relative to spores of *B. thuringiensis, B. cereus, B. pumilis, B. subtilis*, and *B. megaterium*. Thus the invention also provides for the use of the antibody, as well as alternative forms thereof, to differentially detect *B. anthracis* spores from other *Bacillus* spores.

The 23a-14G9 antibody was also tested against spores of 12 virulent *B. anthracis* isolates from geographically diverse regions of the world (USA, Canada, China, Germany, South Africa, United Kingdom, Brazil, Turkey, Australia, and Namibia). The isolates were from both human and animal sources and are listed in Table 1 below. All virulent spore preparations tested strongly positive with 23a-14G9 as the detector antibody and rabbit polyclonal anti-*B. anthracis* IgG as the capture antibody.

TABLE 1

| Isolate # | Original ID | Origin | Source |
|---|---|---|---|
| A0308 | 91-382C-1 | Canada (AB) | Bovine |
| A0033 | 23/32 | China | Wool |
| A0286 | 22 | Turkey (Sivas) | Human |
| A0328 | A30 | Germany (Hessen) | Pig |
| A0446 | 11749 | Namibia (Etosha NP) | Elephant |
| A0462 | 11963 | CAMR/Porton UK | Not reported |
| A0220 | 97-1946/2 | Australia (Victoria) | Bovine blood |
| A0435 | K3 | South Africa (Kruger NP) | Kudu |
| A0248 | #28 | USA (OH) | Human |
| A0488 | Vollum | UK VOLLUM | Not reported |
| A0442 | K88 | South Africa (Kruger NP) | Kudu |
| A0067 | Asc 65 | Brazil | Milk |

The monoclonal antibody of the invention may be referred to as being "specific for" or "specifically immunoreactive with" *B. anthracis* spores. These terms refer to the ability of the antibody to react in a binding reaction to *B. anthracis* spores, or the cognate antigen found in these spores. The reaction can be determinative of the presence or amount of *B. anthracis* spores in the presence of other proteins, spores, or cells. Under assay conditions as desired by the skilled practitioner, including the non-limiting conditions disclosed herein, the antibody binds preferentially to *B. anthracis* spores, or the cognate antigen found therein, and does not bind in a significant or detectable manner to other factors in a sample. Preferred embodiments of the invention utilize conditions wherein the antibody, or an alternative form thereof, selectively binds to produce a signal which is at least twice, preferably at least 10 times to 100 times, background signal or noise. Background signal or noise may include low level cross reactivity with other spores, such as those of *B. thuringiensis* subsp. *Kurstaki.*

In additional embodiments, the invention provides antibodies that recognize or bind the spore specific antigen of *B. anthracis* bound by the 23a-14G9 antibody. For some antibodies, the binding may be specific for the antigen. For other antibodies, the binding may be to an epitope present in a complex of the spore specific antigen bound to the 23a-14G9 antibody. Alternatively, the antibodies may simply bind the 23a-14G9 antibody, but of course those would not be used based on their binding to a spore specific antigen, but rather based upon their ability to bind and thus detect, the 23a-14G9 antibody. Thus such 23a-14G9 binding antibodies may be used as secondary antibodies that bind 23a-14G9 to detect its presence, such as in a complex with its cognate *B. anthracis* spore specific antigen.

Alternative forms of the spore specific antigen binding antibodies of the invention and the 23a-14G9 monoclonal antibody, which is of the IgG class, can be readily produced by methods known in the art. The ability to produce antigen binding fragments of antibodies is well known and may be utilized to produce bivalent $F(ab')_2$ and monovalent Fab fragments for use as disclosed herein. As used herein, "Fab" refers to double chain binding fragments of antibodies comprising at least functionally complete light and heavy chain variable domains. Additionally, methods for the production of hybrid, chimeric, altered, recombinant (including single chain), or humanized forms of antibodies are also known in the art. These antibody forms may be considered derivatives of the monoclonal antibody disclosed herein.

Additional derivative forms include antibodies of the invention, and alternative forms thereof, that have been conjugated to other chemical moieties. Non-limiting examples include a labeled antibody or an alternative form thereof. The term "label", "detectably labeled" or "labeled with a detectable marker" refer to an antibody composition capable of producing a detectable signal indicative of the presence of the labeled molecule. Suitable labels include radioisotopes, a dye, colloidal gold or a similarly detectable marker, nucleotide chromophores, enzymes, substrates, fluorescent molecules, chemiluminescent moieties, magnetic particles, bioluminescent moieties, and the like, including labels suitable for indirect detection, such as biotin. As such, a label is any composition detectable by spectroscopic, photochemical, biochemical, immunochemical, electrical, optical or chemical means. A label may be attached by use of a chemical linker. Exemplary labels are those that produce a visible signal that can be detected by visual inspection.

The antibodies of the invention and alternative forms thereof may also be conjugated by known methods and means to a solid phase support such as, but not limited to, glass, plastic, a synthetic membrane. Other non-limiting examples include beads, particles, dipsticks, fibers, filters, Petri dishes, ELISA (enzyme-linked immunosorbent assay) plates, microtiter plates, silane or silicate supports such as glass slides, and dishes, wells or containers, as well as the sides thereof. Such immobilized forms of the antibodies may be used in the detection methods disclosed herein. They may also be used for immunoaffinity chromatography of *B. anthracis* protein or spores.

The antibodies of the invention and alternative forms thereof may also be formulated into compositions. The compositions may further comprise one or more other reagent for the detection of *B. anthracis* or other *Bacillus* species. Non-limiting examples include complexes of the antibody bound to its cognate *B. anthracis* spore specific antigen and combinations of the antibody with other reagents for use in antibody based detection methods. Other examples include mixtures with other *B. anthracis* binding antibodies or detection agents. Combinations of the antibodies, and alternative forms thereof, with other detection agents may also be part of articles of manufacture, such as testing devices, used to detect *B. anthracis*.

The methods used to detect the presence of *B. anthracis* spores are not limited by design. Non-limiting examples include methods utilizing the antibodies of the invention, and alternative forms thereof as described herein, and based upon the principles of Western blotting or other immunoblotting, ELISA, lateral flow devices, sandwich assays, visual observation by microscopy, competitive and non-competitive immunoassays, immunoenzymetric assays, immunofluorescence, immunomagnetic selection, and flow cytometry (including detection by polychromatic flow cytometry). Additional immunoassay formats are described by Harlow and Lane (1988) *Antibodies, A Laboratory Manual*, Cold Spring Harbor Publications, New York. The methods of the invention are used to qualitatively or quantitatively detect the presence or absence of *B. anthracis* spores in a sample or "test sample".

As used herein, a "sample" or "test sample" refers to a sample isolated from an individual infected with, or suspected of being infected with, *B. anthracis* spores as well as environmental samples suspected of containing *B. anthracis* spores. Alternatively, the terms refer to samples known to contain *B. anthracis* spores for use as a control in the detection methods of the invention or for use in the disclosed detection methods to confirm the presence of, or quantify the amount of, *B. anthracis* spores. The sample may be collected by any appropriate means, including sampling of the outer skin or hair, as well as clothing, in cases of a animal or human subject, and sampling of air, paper, soil, or other solid objects in cases of an environmental sample, such as that from a site suspected to contain *B. anthracis* spores. Medical samples also include sampling or swabbing of a subject's bodily surfaces, including, but not limited to, nasal and oral cavities. Other sample forms include samples of water or food. A sample may also be a powder or granulated material suspected of containing *B. anthracis* spores. A sample of the invention may also be an extract of *B. anthracis* spores or extract of material containing spores or suspected of containing *B. anthracis* spores. In some embodiments of the invention, a sample may be diluted with a sample diluent before being assayed. The diluent may be any suitable solvent as desired by the skilled person.

In cases of air or gas samples, a cyclonic collection device may be used to collect the sample as a non-limiting example. Such a device collects a volume of air or gas and deposits particulates contained therein to a moist surface or liquid medium.

In one embodiment, the invention provides a detection method based on the use of a capture reagent which binds *B. anthracis* spores to form a complex therewith. The capture reagent may be the monoclonal antibody, or alternative forms thereof, as described herein. Alternatively, the reagent may be another antibody which binds *B. anthracis* spores, including, but not limited to, polyclonal or recombinant antibodies that bind a plurality of *Bacillus* spores and cells. In another embodiment, the capture reagent binds at least the spores of *B. thuringiensis, B. cereus, B. pumilis, B. subtilis*, and *B. megaterium* in addition to *B. anthracis*. The capture reagent may be immobilized on a solid phase support, optionally prior to contact with *B. anthracis* spores, as described herein for antibodies of the invention. The reagent need not bind the same epitope as that bound by the 23a-14G9 antibody of the invention. Of course capture agents that bind a complex of the spore (or spore specific antigen) and a spore specific antibody, rather than the antibody alone, may also be used in the practice of the invention.

Whether used with a capture reagent or not, the invention also provides for a detection agent that binds *B. anthracis* spores to directly or indirectly indicated their presence or amount. The detection agent is preferably an antibody of the invention, or an alternative form thereof, which binds the spore specific antigen bound by 23a-14G9. Upon binding, the detection agent forms a bound complex with its binding partner. The detection agent may be detectably labeled such that the presence or amount of the cognate binding partner, and thus *B. anthracis* spores, is signaled by the label after binding of the detection agent. Alternatively, the detection agent is itself bound by a detectably labeled secondary agent. As a non-limiting example where the detection agent is 23a-14G9, a detectably labeled anti-murine IgG antibody may be used to detect 23a-14G9 and thus *B. anthracis* spores.

When used in combination with a capture reagent, a sandwich complex comprising the reagent, a *B. anthracis* spore or spore extract component, and the detection agent is formed. This sandwich complex may be preceded by formation of a complex comprising the capture reagent and a *B. anthracis* spore or spore extract component, which complex is exposed to the detection agent to form the sandwich complex. Alternatively, the sandwich complex may be preceded by formation of a complex comprising the detection reagent and a *B. anthracis* spore or spore extract component, which complex is subsequently exposed to the capture reagent to form the sandwich complex. The specificity of the sandwich complex, as well as other formats, can be introduced by either the capture reagent, the detection reagent, or both. Thus embodiments of the invention include use of the following combinations:

| Capture reagent | Detector reagent |
|---|---|
| Polyclonal antibodies that bind the spore specific antigen, optionally binding other antigens | Monoclonal antibody that binds the spore specific antigen |
| Polyclonal antibodies that bind a complex comprising the spore specific antigen, optionally binding other antigens | Monoclonal antibody that binds the spore specific antigen |
| Monoclonal antibody that binds the spore specific antigen | Polyclonal antibodies that bind the spore specific antigen, optionally binding other antigens |
| Monoclonal antibody that binds the spore specific antigen | Polyclonal antibodies that bind a complex comprising the spore specific antigen, optionally binding other antigens |
| Monoclonal antibody that binds the spore specific antigen | Monoclonal antibody that binds the spore specific antigen |

The methods of the invention, with or without the use of a sandwich format, advantageously detect the presence of *B. anthracis* spores, or the cognate binding partner of the 23a-14G9 antibody, at concentrations at least above 0.02 μg/ml. In other embodiments, the methods detect concentrations above 0.08, above 0.30, above 0.5, above 1, or above 1.25 μg/ml. Alternatively, the methods of the invention may be used to detect the presence of *B. anthracis* spores at concentrations of at least $10^{10}$, at least $10^9$, at least $10^8$, at least $10^7$, at least $10^6$, or at least $10^5$ cfu/ml by analysis of an aliquot of a sample, or diluent thereof, containing spores at such concentrations.

Non-limiting examples of aliquot volumes include 500 μl, 450 μl, 400 μl, 350 μl, 300 μl, 250 μl, 200 μl, or 150 μl sample sizes.

The detection methods of the invention may also include competitive binding assays as embodiments. These comprise the use of a labeled form of *B. anthracis* spores or spore extract components that compete for binding to a detection agent and/or capture reagent as described herein and analogous to competitive assay methods known in the art. The methods provided by the present invention may also be automated in whole or in part.

The materials for use in the methods of the present invention are ideally suited for preparation of kits produced in accordance with well known procedures. The invention thus provides kits comprising agents for the detection and/or quantitation of *B. anthracis* spores, or extracts or disrupted forms thereof, in a sample as described herein. Such kits optionally comprising the agents and/or reagents with an identifying description or label or instructions relating to the use of the kits, or the suitability of the kits, in the methods of the present invention, is provided. Such a kit may comprise containers, each with one or more of the various agents and/or reagents (optionally in concentrated form) utilized in the methods, including, for example, detection agents and/or pre-immobilized forms of capture reagents. A set of instructions or reagent identifiers will also typically be included. Other exemplary kits contain a device or solid phase supports, such as, but not limited to a lateral flow device, a test strip, beads, a membrane, or coated surfaces of a container, dish or well, for the practice of the invention.

The kits may also optionally include a control sample, such as a known sample of immunoreactive *B. anthracis* spores, or the cognate antigen bound by the detection agent and/or capture reagent. A control can be present in known quantities for dilution with the sample diluent used to dilute a sample and used as an external control or added to an actual sample and used as an internal control, optionally for use to determine the sensitivity of the assay in the context of the sample type being tested. The kits can comprise materials for a single assay or for multiple assays.

The invention further provides a hybridoma cell that produces the 23a-14G9 antibody. The cell was deposited with the ATCC on May 19, 2004 and identified by ATCC accession number PTA-6004. The hybridoma may be cultured in vitro to produce antibodies for use as disclosed herein, after an optional isolation step. Alternatively, the hybridoma may be introduced into an animal to form an ascites from which antibody containing fluid may be obtained. The resultant antibodies may be used as disclosed herein, after an optional isolation step. "Isolation" refers to preparation of a composition that predominantly contains the antibodies such that they are present, on a molar basis, more abundantly than other non-solvent entities in a composition. Preferably, "isolated antibodies" contain at least about 50, at least about 60, at least about 70, at least about 80, or at least about 90 percent on a molar basis antibodies relative to non-solvent entities. Isolation may be conducted by purification of antibodies to near, or essentially, homogeneity by removal of contaminating molecular entities.

Additional monoclonal antibodies can be produced in the manner used to produce 23a-14G9. Briefly, mice were exposed to *B. anthracis* spores to generate an immune response and the production of antibodies. Antibody expressing cells were isolated and fused to selectable immortalized cells followed by screening for cells expressing antibodies specific for *B. anthracis* spores. Populations of positive cells were cloned by limiting dilution and further selected to obtain the hybridoma cell line that produces 23a-14G9.

Figure 3:
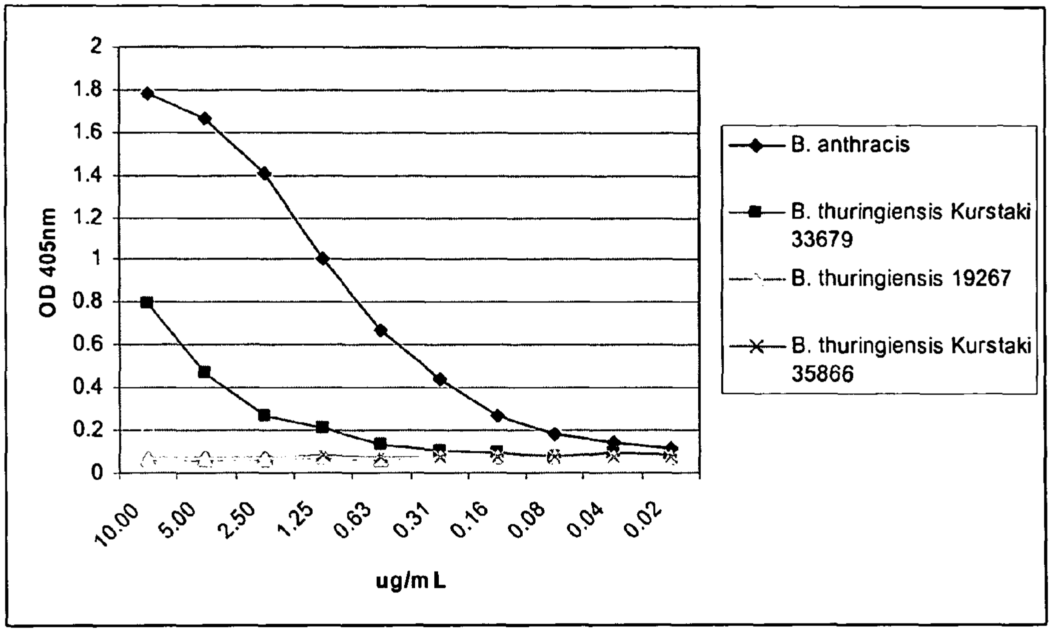
FIG. 3 shows that 23a-14G9 has partial cross reactivity with spores of one isolate of *B. thuringiensis* (subsp. *Kurstaki* ATCC 33679). Generally, use of 23a-14G9 to detect *B. anthracis* produces a signal that is at least about double that of the *Kurstaki* isolate.

Additional antibodies may be produced by use of a complex of an antibody bound to the *B. anthracis* spore specific antigen recognized by the 23a-14G9 antibody. As a non-limiting example, and with reference to FIG. 3, Part A, a complex of the 23a-14G9 antibody bound to its cognate spore specific antigen is used to immunize an animal, such as in combination with a suitable adjuvant known in the field, to produce antibodies against the complex. The animal may be any known in the field for the production of antibodies, including mice, rats, rabbits, and goats. In some embodiments, the use of BALB/C mice with the 23a-14G9 containing complex provides the advantage of reducing, or eliminating, the production of antibodies that bind only to 23a-14G9 because it was produced in BALB/C mice. Thus 23a-14G9 would be recognized as "self" in BALB/C mice. This provides the benefit of increasing the production of antibodies against the spore specific antigen rather than the 23a-14G9 antibody.

The resultant antibodies may be used as polyclonal antibodies that bind the complex. Thus in some embodiments, the polyclonal antibodies may be used as "capture antibodies" for the complex. Such polyclonal antibodies are a heterogeneous population that includes at least 1) antibodies that bind an epitope of the 23a-14G9 antibody, 2) antibodies that bind an epitope of the spore specific antigen exposed in the complex, and 3) antibodies that bind an epitope of the complex but not found in either the 23a-14G9 antibody or the antigen. The heterogeneous population may be fractionated based on the heterogeneity. As a non-limiting example, the antibodies may be affinity purified against the 23a-14G9 antibody to produce polyclonal antibodies that bind epitopes of the antigen or the complex but not the 23a-14G9 antibody itself.

Figure 4:
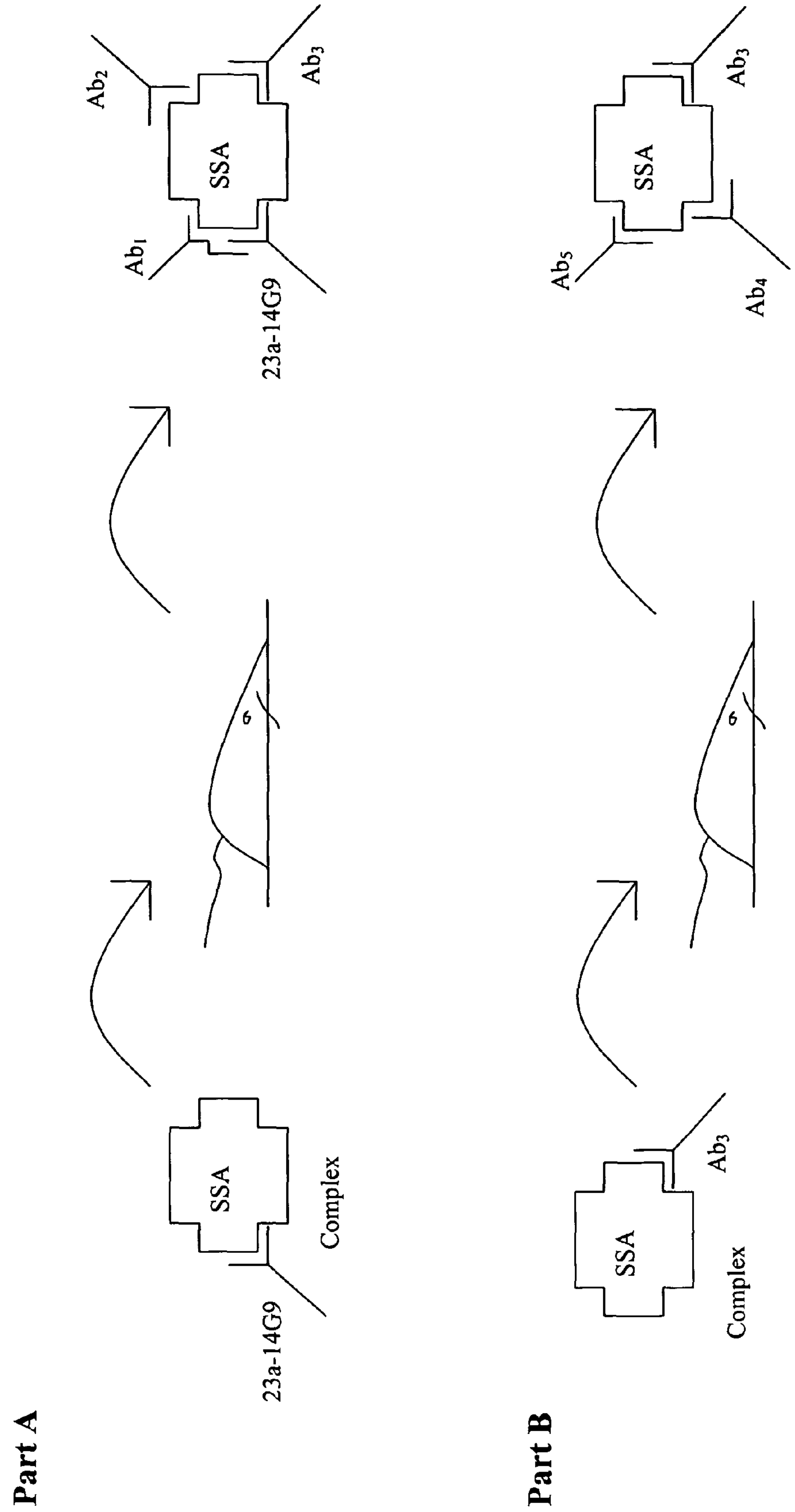
FIG. 4 illustrates a methodology for producing antibodies of the invention. Part A shows the use of a complex of the 23a-14G9 antibody and spore specific antigen (SSA) to immunize an animal. The animal then produces antibodies of the invention as described herein. Representative antibodies include $Ab_1$, which binds a region defined by both 23a-14G9 and the SSA, $Ab_2$, which binds a first portion of the SSA not bound by 23a-14G9, and $Ab_3$, which binds a second region of the SSA not bound by 23a-14G9. Part B shows the use of a complex containing $Ab_3$ and SSA as an immunogen introduced into an animal to generate additional antibodies of the invention. Representatives antibodies include $Ab_4$, which binds a region of the SSA available in the absence of the 23a-14G9 antibody, and $Ab_5$, which binds a portion of the SSA in common with $Ab_1$. It is of course possible that a process like that shown in Part B would regenerate the 23a-14G9 antibody or produce another antibody that binds the same epitope as 23a-14G9.

Cells that produce the heterogeneous population may also be screened to select antibodies that bind one of the three fractions described above. As a non-limiting example, the cells may be used to form hybridomas by methods known in the field that are then screened against the 23a-14G9 antibody to select hybridomas that produce antibodies that bind the 23a-14G9 antibody from hybridomas expressing antibodies that bind the spore specific antigen or that bind the complex. Similarly, the hybridomas can be screened to identify those expressing antibodies that bind *B. anthracis* spores rather than either the 23a-14G9 antibody or the complex used to produce the heterogeneous population. This may be used to obtain hybridomas expressing antibodies that are specific for the spore specific antigen bound by 23a-14G9. Of course such antibodies may be used in the same manner as 23a-14G9 as described herein, including use to generate additional antigen binding antibodies. See FIG. 4, Part B.

Additionally, the antibodies and/or hybridomas may be screened against any *Bacillus* strains or spores or other molecules to which cross reactivity is detected. This allows for the selection of antibodies which would be specific, or more specific, for *B. anthracis* relative to the other to the cross reacting strain or other molecule. In some embodiments of the invention, antibodies or hybridomas are selected relative to spores of *B. thuringiensis* subsp. *Kurstaki*, such as ATCC 33679, which has low level cross reactivity with the 23a-14G9 antibody. Selection relative to ATCC 35866 may also be performed.

Antibodies that bind the complex may also be selected based upon binding to the complex to the exclusion of binding to 23a-14G9 and *B. anthracis* spores. Such antibodies may be advantageously used to bind or detect the complex, such as when used as a capture reagent to immobilize the complex.

Having now generally described the invention, the same will be more readily understood through reference to the following examples which are provided by way of illustration, and are not intended to be limiting of the present invention, unless specified.

EXAMPLES

Example 1

23a-14G9 Recognizes a Spore-Specific Antigen

Materials and Methods (1) Antigen Preparation

Spores:

*B. anthracis* was grown in confluent cultures on TSA plates for 3 days to allow sufficient time for vegetative cells to deplete essential nutrients from the medium resulting in spore formation. Bacteria/spores were washed off plates in sterile phosphate buffered saline (PBS) and incubated at 60° C. in a water bath for 1 hour to kill remaining vegetative cells while spores remain unaffected. Spores were then washed two times by centrifugation at 3400 rpm for 10 minutes at 4° C. An aliquot of the preparation was stained with malachite green to visualize spores to verify that the preparation contained a preponderance of spores, with very few vegetative cells present.

Vegetative Cell Antigens:

*B. anthracis* vegetative cells were cultured overnight in an aerated liquid culture. Vegetative cells were pelleted by centrifugation, washed, and then lyzed in a TRIS-EDTA buffer solution containing high salt and detergent. The supernatant was dialyzed against PBS.

(2) Capture ELISA

For the capture ELISA, protein G-purified rabbit polyclonal IgG from rabbits immunized with *B. anthracis* spores and vegetative cells was used as capture antibody and coated unto ELISA plates at a concentration of 10 μg/ml. The ELISA plates were blocked with a blocking solution containing 5% skim milk according to standard procedures. Two fold-serial dilutions of either spore or vegetative cell antigens were incubated in the ELISA plate for 1 hour. The plates were extensively washed, followed by addition of monoclonal antibody (mAb) 23a-14G9 at 10 μg/ml, and incubation for 1 hour. Plates were extensively washed. Development of the ELISA reaction was initiated with goat anti-mouse IgG antibody conjugated with horse radish peroxidase, followed by addition of the substrate ABTS. Plates were read in an ELISA plate reader at an OD of 405 nm.

Results

Results are presented in FIG. 1, which clearly demonstrates that 23a-14G9 reacts strongly with *B. anthracis* spore antigens but does not react at all with antigens present in vegetative cells of *B. anthracis*. Thus, 23a-14G9 is a monoclonal antibody which recognizes a spore-specific antigen of *B. anthracis.*

Example 2

Specificity of 23a-14G9

The specificity of *B. anthracis* spore-specific monoclonal antibody 23a-14G9 is illustrated as follows. A capture ELISA was performed utilizing rabbit polyclonal IgG as the capture antibody and the *B. anthracis* spore-specific monoclonal antibody 23a-14G9 as the detector antibody. Spores from the following *Bacillus* organisms were used as antigens: *B. anthracis* Sterne; *B. thuringiensis* ATCC 35646; *B. cereus* ATCC 33018; *B. pumilis* ATCC 72; *B. subtilis* ATCC 6051; and *B. megaterium* ATCC 25833.

Figure 2:
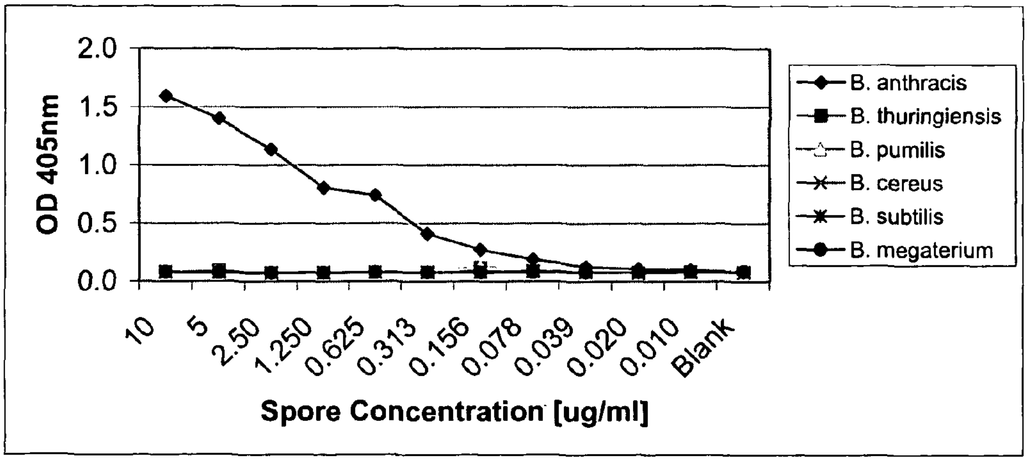
FIG. 2 shows the specificity of 23a-14G9 for *B. anthracis* spores relative to other *Bacillus* spores.

As shown in FIG. 2, monoclonal antibody 23a-14G9 reacted only with spores of *B. anthracis*. The antibody did not react with spores of *B. thuringiensis, B. cereus, B. megaterium, B. pumilis*, or *B. subtilis*. Thus, monoclonal antibody 23a-14G9 is specific to *B. anthracis* and can be used to detect and differentiate *B. anthracis* spores from other *Bacillus* spores.

Using the same conditions, the 23a-14G9 antibody was tested against spores of the following *Bacillus* isolates: *B. cereus* ATCC 9620, *B. cereus* ATCC 14579 (type strain), *B. cereus* ATCC 49064, *B. cereus* ATCC 10702, *B. cereus* ATCC 7004, *B. cereus* ATCC 33019, *B. thuringiensis* ATCC 19267, *B. thuringiensis* ATCC 10792, *B. thuringiensis* subsp. *Israelensis* ATCC 39152, *B. thuringiensis* subsp. *Kurstaki* ATCC 33679, and *B. thuringiensis* subsp. *Kurstaki* ATCC 35866. The antibody was negative against all of these *B. cereus* isolates and *B. thuringiensis* isolates, except ATCC 33679 which was partially cross-reactive (see FIG. 3). ATCC 33679 was positive above an antigen concentration of 2.5 μg/ml vs. 0.04 μg/ml for *B. anthracis.*

All references cited herein, including patents, patent applications, and publications, are hereby incorporated by reference in their entireties, whether previously specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A monoclonal antibody produced by the hybridoma cell line deposited with the ATCC on May 19, 2004 and identified by ATCC accession number PTA-6004.

2. A composition comprising the monoclonal antibody of claim 1.

3. A fragment of the antibody of claim 1, wherein said fragment binds the spores of *Bacillus anthracis.*

4. The fragment of claim 3 wherein said fragment is a bivalent $F(ab')_2$ fragment, or a monovalent Fab fragment.

5. A hybrid, chimeric, recombinant, or humanized form of the monoclonal antibody of claim 1, wherein said form of the antibody binds the spores of *Bacillus anthracis.*

6. A method to detect the presence or absence of *Bacillus anthracis* spores in a sample, said method comprising detecting the binding of an antibody according to claim 1 to a component of said sample, to form a bound complex, after said sample is contacted with said antibody.

7. The method of claim 6 wherein said antibody is able to bind *Bacillus anthracis* spores.

8. The method of claim 6 wherein said sample is suspected of containing *Bacillus anthracis* spores.

9. The method of claim 6 wherein said component is bound to a capture reagent, optionally immobilized on a solid support, and said monoclonal antibody is detectably labeled.

10. The method of claim 9 wherein said capture reagent is an antibody.

11. The method of claim 9 wherein said capture reagent is a polyclonal antibody that binds *Bacillus anthracis* spores.

12. The method of claim 11 wherein said capture reagent also binds spores of *Bacillus thuringiensis, Bacillus cereus, Bacillus pumilis, Bacillus subtilis*, and *Bacillus megaterium.*

13. The method of claim 6 wherein the method detects said component at concentrations at least above 0.02 μg/ml.

14. The method of claim 6 wherein said detecting further comprises contacting the bound complex with a detectable agent that binds said component or said complex.

15. A kit for detecting the presence or absence of *Bacillus anthracis* spores in a sample, said kit comprising the monoclonal antibody of claim 1.

16. A complex comprising an antibody of claim 1 bound to a spore specific antigen of *Bacillus anthracis*.

17. A method to detect the presence or absence of *Bacillus anthracis* spores in a sample, said method comprising detecting the binding of an antibody fragment according to claim 3 to a component of said sample, to form a bound complex, after said sample is contacted with said antibody fragment.

18. A method to detect the presence or absence of *Bacillus anthracis* spores in a sample, said method comprising detecting the binding of an antibody fragment according to claim 4 to a component of said sample, to form a bound complex, after said sample is contacted with said antibody fragment.

19. A method to detect the presence or absence of *Bacillus anthracis* spores in a sample, said method comprising detecting the binding of an hybrid, chimeric, altered, recombinant, or humanized antibody according to claim 5 to a component of said sample, to form a bound complex, after said sample is contacted with said hybrid, chimeric, recombinant, or humanized antibody.

* * * * *